(12) United States Patent
Gatti et al.

(10) Patent No.: US 6,284,738 B1
(45) Date of Patent: Sep. 4, 2001

(54) INJECTABLE READY-TO-USE SOLUTIONS CONTAINING AN ANTITUMOR ANTHRACYCLINE GLYCOSIDE

(75) Inventors: Gaetano Gatti, Sesto San Giovanni; Diego Oldani, Robecco sul Naviglio; Giuseppe Bottoni, Bergamo; Carlo Confalonieri, Cusano Milanino; Luciano Gambini, Cornaredo; Roberto De Ponti, Milan, all of (IT)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/149,360

(22) Filed: Sep. 8, 1998

Related U.S. Application Data

(60) Continuation of application No. 07/827,742, filed on Jan. 29, 1992, now Pat. No. 6,107,285, which is a division of application No. 07/503,856, filed on Apr. 3, 1990, now Pat. No. 5,124,317, which is a division of application No. 07/385,999, filed on Jul. 27, 1989, now Pat. No. 4,946,831, which is a continuation of application No. 06/878,784, filed on Jun. 26, 1986, now abandoned.

(30) Foreign Application Priority Data

Aug. 2, 1985 (GB) .................................................. 8519452

(51) Int. Cl.[7] .................................................. A61K 31/70
(52) U.S. Cl. .............................................. 514/34; 536/6.4
(58) Field of Search .................................. 514/34; 536/6.4

(56) References Cited

U.S. PATENT DOCUMENTS

| 4,105,076 | 8/1978 | Henry et al. .............................. 536/4 |
| 4,296,105 | 10/1981 | Bauran et al. ........................ 424/180 |

FOREIGN PATENT DOCUMENTS

| 1005760 | 2/1977 | (CA) . |
| 1041488 | 10/1978 | (CA) . |
| 1046507 | 1/1979 | (CA) . |
| 1046508 | 1/1979 | (CA) . |
| 1204738 | 5/1980 | (CA) . |
| 1129344 | 8/1982 | (CA) . |
| 1203482 | 4/1986 | (CA) . |
| 2014244 | 10/1990 | (CA) . |
| 35 36 896 | 4/1986 | (DE) . |
| 0 401 896 A1 | 12/1990 | (EP) . |
| 2405957 | 5/1979 | (FR) . |
| 2178311 | 2/1987 | (GB) . |

OTHER PUBLICATIONS

Beijnen et al (1985), "Stability of Anthracycline Antitumor Agents in Infusion Fluids," J Parenteral Science and Technology vol. 39 pp. 220–222.

The Merck Index (1983), "Doxorubicin." 10th Edition. AN–3435 p. 499.

Kano et al. Electrochemical Properties of Adnamycin Adsorbed on a Mercury Electrode Surface. The Chemical Society of Japan Bull Chem Soc Jpn. 57. 2383–2390 (1984).

Kano et al., The Effects of the pH and the Temperature on the Oxidation–reduction Properties of Adnamycin Adsorbed on a Mercury Electrode Surface. The Chemical Society of Japan Bull Chem Soc. Jpn. 58. 424–428 (1985).

Beijnen et al (1986). "Aspects of Degradation Kinetics of Daunorubicn in Aqueous Solution," International J Pharmaceutics, vo. 31 pp 78–82.

Beijnen et al. (1986). "Aspects of the Degradation Kinetics of Doxuribicin in Aqueous Solution" International J Of Pharmaceutics vo. 32 pp. 123–131.

Bosanquet, A G (1986). "Stability of Solutions of Antineoplastic Agents During Preparation and Storage For in Vitro Assays" Cancer Chemother Pharmacol., vol. 17, pp. 1–10.

Daugherty et al (1981). "Photolytic Destruction of Adnamycin" J. Pharm Pharmacol. vol. 33. p. 556.

Dorr and Fntz (1980). "Doxorubicin." Cancer Chemotherapy Handbook Elsevier. New York. pp. 388–401.

Eksborg and Ehrsson (1984). "Liquid Chromatography in Anticancer Drug Research with Special Reference to Anthraquinone Gycosides" J Pharmaceutical & Biomedical Analysis, vol. 2 pp. 297–303.

Eksborg, S (1978). "Extraction of Daunorubicin and Doxorubicin and Their Mycrox Metabolites Self–Association in Aqueous Solution" J Pharmaceutical Sciences, vol. 67, pp. 782–785.

Flora et al (1980). "The Loss of Paraben Preservatives During Freeze Drying." J. Pharm Pharmacol. vol. 32. pp. 577–578.

Florence and Atwood (1981). "Physicochemical Principles of Pharmacy" MacMillan Press. London. p. 475.

Garnick et al (1983). "Clinical Evaluation of Long–Term, Continuous–Infusion Doxuribicin" Cancer Treatment Reports vol. 67 pp. 132–142.

Henry, D W (1976). "Adnamycin." Cancer Chemotherapy. American Chemical Society Symposium Senes. pp. 15–57.

(List continued on next page.)

*Primary Examiner*—Elli Peselev
(74) *Attorney, Agent, or Firm*—McDonnell Boehnen Hulbert & Berghoff

(57) ABSTRACT

According to the invention there is provided a sterile, pyrogen-free, ready-to-use solution of an anthracycline glycoside, especially doxorubicin, which consists essentially of a physiologically acceptable salt of an anthracycline glycoside dissolved in a physiologically acceptable solvent therefor, which has not been reconstituted from a lyophilizate and which has a pH of from 2.5 to 6.5. The solution of the invention is particularly advantageous for the administration by injection of the anthracycline glycoside drugs, e.g. doxorubicin, in the treatment of both human and animal tumors.

19 Claims, No Drawings

OTHER PUBLICATIONS

Hoffman et al. (1979) "Stability of Refrigerated and Frozen Solutions of Doxorubicin Mycrochloride." Am J Hosp. Pharm. vol. 29 1536–1538.

Janssen et al (1985). "Doxorubicin Decomposition on Storage Effect of pH. Type or Buffer and liposome Encapsulation," International Pharmaceutics. vol. 23, pp. 1–11.

Jonkman–de Vnes et al (1994). "Pharmaceutical Development of a Parental Lyophilized Formulation of the Nove Indoloquinone Antitumor Agent EO9" Cancer Chemother Pharmacol. vol. 34. pp. 416–422.

Kaniewska, T (1978). "Study of the Decomposition of Adnamycin" Chemical Abstracts vol. 88 No. 197526x p 395.

Kaniewska, T (1977). "A Study of Decomposition of Adnamycin." Pharmacia Polska. vol. 9. 539–542 (English translation attached).

Ketchum et al. (1981). "Cost Benefit and Stability Study of Doxorubicin Following Reconstitution." Am J Intravenous Therapy & Clinica Nutrition, vol. 8, pp. 15–18.

Kristensen and Moller (1983). "Alman Farmaci II." Dansk Farmaceuttoreings Forlag Kobenhavn. pp. 408. 442 447 (English translation attached).

Martindale (1982). "Doxorubicin Hydrochloride." The Extra Pharmacopeia, Antineoplastic Agents and Immunosuppressants 26th Edition The Pharmaceutical Press. London. J E F Reynolds. Ed. pp. 205–208.

Masuike et al (1984) "Determination of Adnamycin and its Metabolites in Biological Samples Using High Performance Liquid Chromatography I Analysis of Serum and Plasma by Direct Injection Method"Yakugaku Zasshi vol. 104. 614–615 ;English abstract).

Europaischez Arzneibuch. vol. III. 1979. p. 654 (English translation attached).

Arcamone et al (1972). "Structure and Physiochemical Properties of Adnamycin (Doxorubicin)," International Symposium on Adnamycin Springer–Verlag Berlin. pp. 9–22.

Beijnen, J M et al (1985). Aspects of the Chemcial Stability of Doxorubicin and Seven Other Anthracyclines in Acidic Solution Pharmaceutiscn Weekblad Scientific Edition. vol. 7 pp. 109–115.

German Patent Office Decision dated Oct. 8, 1998 (English translation attached) revoking Patent No. 36 21844.

Wang and Kowal (1980). "Review of Excipients and pris for Parenteral Products Used in the United States." *J. of the Parenteral Drug Association.* vol. 14. p. 452–462.

Hams, Daniel C (1995). "Quantitative Chemical Analysis," $4^{th}$ Edition. W H. Freeman and Company.

Arcamone et al (1969). "Adnamycin, 14–Hydroxydaunomycin, a New Antitumor Antibiotic from *S Peucetius Var Caesius*" *Biotechnology and Bioengineering.* vol. XI. pp. 1101–1110.

Despois et al. (1967). "Isolement D'un Nouvel Antibiotique Doue D'Activite Antitumorale. La Rubidomycine 113 057 R P J Identite De Rubidomycine et de La Daunomycine." *Path Biol.*, vol. 15, pp. 887–891.

Lokich et al (1983), "Constant Infusion Schedule for Adrimvein A Phase I–II Clinical Trial of a 30–Day Schedule by Ambulatory Pump Delivery System." *J. Clinical Oncology*, vol. 1, pp. 24–28.

Wasserman and Bundgaard (1983), "Kinetics of the Acid–Catalyzed Hydrolysis of Doxorubicin." *International J Pharmaceutics.* vol. 14, pp. 73–78.

Merck Index (1996), Mitoxantrone, 12th Edition. Entry 6303, p. 1064.

Martindale (1989), Mitotone. *The Pharmaceutical Press*, 29th Edition, London. Entry 1852x. pp. 643–645.

ABPI Data Sheet Compendum. 1994–1995. "Novantron Injection." Lederle Laboratories pp. 752–754.

Geigy Scientific Tables vol. 3 *Physical Chemistry Composition of Binod Hematology Somatormetric Data*, 8th revised and enlarged edition Edited by C Lenmer pp. 54–60.

Dorr (1979). "Incompatibilities with Parenteral Anticancer Drugs." *The American Journal of Intravenous Therapy* Feb./Mar. pp. 42, 45–46, 52.

Beranrd, J., et al. (1969) *Rubidomycin*, Springer–Verlag, Berlin–Heidelberg–New York.

Karlsen, J. et al. (1983). "Stability of Cytotoxic Intravenous Solutions Subjected to Freeze–Thaw Treatment" *Nor Pharm Acta*. vol. 45. pp. 61–67.

Vogelzang, N J, et al (1985), "Phase I Trial of an Implanted Battery–Powered Programmable Drug Delivery System for Continuous Doxorubicin Administration." *Journal of Clinical Oncology*. vol. 5, No. 3 (Mar.). pp. 407–414.

Falk, K. et al (1979), "Mutagenicity in Urine of Nurses Handling Cytostatic Drugs". *The Lancet*. Jun. 9, 1979, pp. 1250–1251.

"Union Warns of Cancer Drug Dangers", *Chemistry and Industry*, Jul. 4, 1983.

Lassila, O., et al. (1980), "Immune Function in Nurses Handling cytostatic Drugs". *The Lancet*, Aug. 30, 1980. p. 452.

*Abstract of Medical Economics Co. Chemistry–Industry*, Feb. 7, 1983, p. 99.

*Chemical Abstract*, vol. 99, p. 345 (1983), Abst. No. 99:218014y.

*Topics in Antibiotic Chemistry*, 2, 109–115, 1978.

Tan, C. et al., Daunomycin, an Anti–Tumor Antibiotic, in the Treatment of Neoplastic Disease, Mar. 1967, *Cancer* 20:333–353.

Samuels, L.D. et al., "Daunorubican Therapy in Advanced Neuroblastoma", Apr. 1971, *Cancer* 27:831–834.

Miller, A.A and Schmidt, C.G., "Clinical Pharmacology and Toxocology of 4"–O–tetrahydropyranyladriamycin", Mar. 1, 1987, *Cancer Research* 47.1461–1465.

Rozencweig, M. et al., "Preliminary Experience with Marcellomycin: Pre–Clinical and Clinical Aspects" P.5499–562.

*The Interpharm International Dictionary of Biotechnology and Pharmaceutical Manufacturing*, edited by Dean E. Snyder, Publisher Buffalo Grove, IL Interpharm Press, Inc., 1992.

Merck Index, $10^{th}$ edition 1983, p. 499, entry 3,435.

Bosanquet, "Stability of solutions of antineoplastic agents during preparation and storage for in vitro assays", *Cancer Chemotherapy and Pharmacology*, vol. 17, 1986, pp. 1–10.

Rolf Kaltofen, Joachim Ziemann et al., *Tabellenbuch Chemie*, $12^{th}$ edition, pp. 172, 181.

Yüksel, "Determination of Ceftriaxone in Aqueouse Humour and Serum Samples by Differential–pulse Adsorptive Stripping Voltammetry", *Analyst*, vol. 119, 1994, pp. 1575–1577.

Falbe et al., *Rompp Chemie Lexikon*, $9^{th}$ edition, Georg Thieme Verlag Stuttgart, New York, 1992. "Buffers", pp. 3677–3678.

Mortimer, *Chemie*, $3^{rd}$ edition, Georg Thieme Verlag Stuttgart. New York. 1980. pp. 490–494.

Young et al., The Anthracycline Antineoplastic Drugs (1981) vol. 305(3) New England J Med 139.

Casazza, Experimental Studies on New Anthracyclines (1984) (Proc of Int Symposium on Adnamycin: Ogawa et al. eds).

Aubel Sadron et al., Daunorubicin and doxorubicin, anthracycline antibiotics, a physicochemical and biological review (1984) Biochemie 66, pp. 333–352.

Abdella et al., A Chemical perspective on the Anthracycline Antitumor Antibiotics, Env. Health Persp. vol. 64, pp. 3–18 (1985).

Arcamone, Daunomycin and Related Antibiotics Topics in Antibiotic Chemistry vol. 2 (Sammes. ed.) (1978).

Brown. Adriamycin and Related Anthracycline Antibiotics, Prog. Med. Chem 15 124 (1978).

Goormagtigh et al., Anthracycline Glycoside–Membrane Interactions, Biochem. Biophys. Acta 271–288 (1984).

Skovsgaard et al., Adrimycin, An Antitumor Antibiotic: A Review with Special Reference to Daunomycin, Dan. Med. Bull 22(2):62 (1975).

Bachur et al., Cellular pharmacodynamics of several anthracycline antibiotics (1976) J. Med Chem 19(5):651.

Suarato, "Antitumor Anthracyclines", *The Chemistry of Antiumour Agents* 1990) (Wilman, ed.).

Legha, "The Anthracyclines and Mitoxantrone", *Cancer Chemotherapy by Infusion* $2^{nd}$ edition (Lokich et.) (1990) Precept Press.

Bouma et al., Anthracycline Antitumor agents: A review of physcicochemical, analytical and stability properties Pharm. Weekblad Sc. Ed., vol. 8, pp. 109 (1986).

Williams, Stability & Compatibility of Admixtures of Antineoplastic Drugs, *Cancer Chemotherapyhy by Infusion.* $2^{nd}$ Edition (Lukich et.) (1990) Precept Press.

Williams et al., Photoinactivation of Anthracyclines (1981) Photochemistry & Photobiology, vol. 34, p. 131.

Poochikian et al., Stability of anthracycline antitumor agents in four infusion fluids (1981) Chemical Abstracts, vol. 94 214489f.

Keusters, et al., Stability of solutions of doxorubicin and epirubicin in plastic mini bags for intravesical use after storage at –20°C and thawing by microwave radiation (1986) Pharm. Weekblad Sc Ed vol. 5 p. 144.

Bekers et al., Effect of cyclodextrins on anthracycline stability in acidic aqueous media (1988) Pharm. Weekblad. S. Ed., vol. 10,207.

Wood, Mary Jayne: Stability of anthracycline cytotoxic agents in solution and infusion fluids—submitted for the degree of Master of Philosophy (The University of Aston in Birmingham). Oct. 1988.

Wood et al., Stability of Doxorubicin, Daunorubicin and Epirubxcin in Plastic Syringes and Minibags (1990) J. Clin. Pharm. Therapeutics vol. 15, p. 279–289.

Crom et al., Pharmacokinetics of Anticancer Drugs in Children, Clin Pharm. 12.pp. 168–213 (1987).

Greidonus, et al, "Continuous Infusion of Low–dose Doxorubicin, Epirubicin and Mitoxantrone", *Cancer Chemotherapy: A Review*, (1988) Pharm. Weekblad. Sci Ed., vol. 10. pp. 237.

Bachur et al., Daunorubicin and adriamycin metabolism in the golden syrian hamster (1973) Biochem. Med. vol. 8, pp. 352.

Haneke et al., Quanititation of Daunorubicin. Doxorubicin, and their Aglycones by Ion–Pair Reversed–Phase Chromatography, J. Pharm. Sci. 70(10) 1112(1981).

Tomlinson et al., Concomitant Adsorption and Stability of Sonic Anthracycline Antibiotics (Oct. 1982) 71 (10) J Pharm Sci. 1121.

Von Hoff et al, Daunomycin An Anthracycline Antibiotic Effective in Acute Leukemia, Adv. Pharm. Chemo. 15:1 (1978).

Cassinelli et al., La Daunomicina: Un Nuovo Antibiotico Ad Attivita Citostatica Isolamento E Proprieta (1963) Giorn Microbial. 11:167.

Arcamone. La Constitution Chimique de la Daunomycine, Path. Biol. 15(19–20): 893 (1967).

Di Marco et al., Daunomycin, a New Antibiotic of the Rhodomycin Group, Nature 201 706(1964).

Angiuli et al, Structure of Daunomycin X–Ray Analysis of N–Br–Acetyl–Daunomycin Solvate, Nature New Biol., 234:78 (Nov. 1971).

Trissel et al; Investigational Drug Information (1978) Drug Intell Clin Pharm vol. 12, p. 404.

Handbook on Injectable Drugs (Trissel) $2^{nd}$ Ed. 1980,p. 562.

Handbook on Injectable Drugs (Trissel) $5^{th}$ Edition (1988), p. 222–223.

AHFS Drug Information 1984, pp. 249–250.

AHFS Drug Information 1990, pp. 501–503.

Fischer et al., The Cancer Chemotherapy Handbook $3^{rd}$ Edition (1989), pp. 65–69.

Drug Information for the Health Care Professional USP DI 1991—$11^{th}$ Edition, pp. 1080–1084.

Beijnen, et al., Structure Elucidation and Characterization of Daunorubicin Degradation Products (1987) Int. J. Pharm., vol. 34, p. 247.

Bachur, Daunomycin Metabolism in Rat Tissue Slices., J. Pharm. Exp Ther 175(2):331.

Riley, et al, Review of New Drugs—1980, U S. Pharm. 33 (Feb. 1981).

Boiron et al., Daunorubicin in the Treatment of Acute Myelocytic Leukemia. The Lancet (Feb. 1969). p. 330.

Di Marco et al., Activity of Adriamycin (NSC 123127) and Daunomycin (NSC 82151) Against Mouse Mammary Carcinoma, Cancer Chemother. Rep., part 1, vol. 56(2). 153 (1972).

Barthelemy–Clavey et al., Self–Association of Daunorubicin, FEBS Lett. vol. 46(1), pp. 5(1974).

Calendi et al., On Physico–Chemical Interactions between Daunomycin and Nucleic Acids Biochem Biophys. Acta., vol. 103:25 (1965).

Schreier, Binding of Daunomycin to Acidic Phospholipids J Par. Sci Tech, vol. 43. No. 4, p. 213 (1989).

Rhone–Paulene S.A, Improvements in or relating to Antibiotics and their Preparation. U.K. Patent 985,598 (Mar. 10, 1965).

Dubost et al., Un nouvel antibiotique a proprieties cytostatiques: la rubidomycine (1963) C R Acad Sci. Paris, 257, pp. 813.

Maral et al., Etude Toxicologique et activite Antitumorale Experimentale de la Rubidomycine (13.057 R.P.) Path. Biol., vol. 15, No. 19–20, pp. 903–908 (1967).

Depois et al: Un nouvel antibiotique dove d'activite antitumorale la rubidomycine (13.057 R.P.). J Preparation et properties, Arzricial Forsch. 17 934 (1967).

Brazhnikova et al., Physicochemical Properties of Antitumor Antibiotic Rubomycin produced by Act Cocruleorubidus (1986) Antibiotki 11 763.

"Discovery & Development of Doxorubicin", *Doxorubicin, Anticancer Antibiotics* (Areamone, eds) (1981) Academic Press, pp. 1–47.

Blum et al, Adriamycin: A New Anticancer Drug with Significant Clinical Activity, Annals of Int. Med., 80:249–259 (1974).

Arcamone et al., Adriamycin (14–Hydroxydaunomycin), a Novel Antitumor Antibiotic Tetrahedron Letters No. 13, pp. 1007–1010.

Di Marco et al., Adriamyicn, a New Antibiotic, Antitumour, Activitiy, Cancer Chem Reports, part 1. vol. 53, No. 1, p. 33 (1969).

Trissel: A Handbook on Injectable Drugs $2^{nd}$ edition (1980), p. 196.

Trissel: A Handbook on Injectable Drugs $4^{th}$ edition (1986), pp. 215–217.

Trissel: A Handbook on Injectable Drugs $5^{th}$ edition (1988), pp. 259–264.

McEvoy, AHFS Drug Information 1984, pp. 251–254.

AHFS Drug Information 1990, pp. 504–507.

Fischer, The Cancer Chemotherapy Handbook $3^{rd}$ edition (1989). pp. 82–87.

Drug Information for the Health Care Professional USP DI (1991) $11^{th}$ Edition, pp. 1217–1222.

Benvenuto et al., Stability & Compatibility of Antitumor Agents in Glass & Plastic Containers. (Dec. 1981). Am. J. Hosp. Pharm., vol. 38, p. 1914.

Walker et al., Doxorubicin Stability in Syringes and Glass Vials and Evaluation of Chemical Contamination, Can J Hosp Pharm 44(2): 71(1991).

Gupta et al., Investigation of the Stability of Doxorubicin Hydrochloride using Factorial Design. Drug Development & Industrial Pharmacy, (1988) vol. 14(12) pp. 1657–1671.

Beijnen et al., Stability of intravenous admixtures of doxorubicin and vincristine. Am J. Hosp Pharm. vol. 43, p. 3022. (Dec. 1986).

Asker et al., Effects of Glutathione on Photolytic Degradation of Doxorubicin Hydrochloride, J Par. Sci. Tech (1988), 42(5)193.

Habib et al., Photostabilization of doxorubicin Hydrochloride with Radioprotective and Photoprotective Agents: Potential Mechanism for Enhancing Chemotherapy during Radiotherapy (Nov.–Dec. 1989) 43 J. Parenteral Science & Technology, vol. 43, No. 6, pp. 254. (Nov.–Dec. 1959).

Speth, et al., Clinical Pharmacokinetics of Doxorubicin, Clin. Pharm., vol. 15, pp. 15–31, (1988).

Yee et al. Adriamycin: A Brief Review (Apr., 1981) Am. J. Int Ther Clin Nut. pp. 7–12.

Hoffman et al., Stability of Refrigerated and Frozen Solutions of Doxorubicin Hydrochloride (Nov. 1979). Am. J. Hosp. Pharm. vol. 36(11) 1536–1538.

Karlsen et al., Stability of cytotoxic intravenous solutions subjected to freeze–thaw treatment (1983), Chemical Abstracts, vol. 99, No. 146022, p. 374.

Gaj., et al., Compatibility of Doxorubicin Hydrochloride and Vinblastine Sulfate—The Stability of a Solution Stored in Corned ® Reservoir Bags or Monoject® Plastic Syringes (May, 1984) Am J IV Ther. Clin Nut, p. 8.

Tavoloni et al., Photolytic Degradation of Adriamycin (1980) Comm. J. Pharm Pharmacol. vol. 32. p. 860.

Garnick et al., Phase 1 Trial of Long Term Continuous Adriamycin Administration, Proc. Am Soc Clin Oncol., C–106: p. 359,(Mar. 1981).

Lokich et al, Constant Infusion Schedule for Adriamycin A Phase I–II Clinical Trial fo a 30–Day Schedule by Ambulatory Pump Delivery System, J. Clin. Oncol., vol. 1(1):24(1983).

Vogelzang et al., Continuous Doxorubicin Infusion (CDI) Using an Implanted Lithium Battery–Powered Drug Administration Device System, Proc Am.Soc. Clin.Oncol C–1030 p. 263, (Mar. 1984).

Legha et al., Reduction of Doxorubicin Cardiotoxicity by Prolonged Continuous Intravenous Infusion. Ann. Int Med., vol. 96, No. 2, p. 133 (1982).

Pavlik et al, Stability of Doxorubicin in Relation to Chemosensitivity Determinations Loss of Lethality and Retention of Antiproliferative Activity (1984). Cancer Investigation 2(6), 449–458.

Dozier et al., Practical Considerations in the Preparation and Administration of Cancer Chemotherapy (Sep. 1983) Am.J. Int. Ther Clin Nut, p. 6.

Kirschenbaum et al Stability of injectable medications after reconstitution, Am J. Hosp Pharm.: 33 767–790 (Aug., 1976).

Janssen et al., Doxorubicin decomposition on storage. Effect of pH, type of buffer and liposome encapsulation, (1985) Chemical Abstracts, vol. 102, No. 209226k.

Crommelin et al, Preparation and characterization of doxorubicin–containing liposomes. II Loading capacity, long-–term stability and of doxorubicin–bilayer interaction mechanism (1983) Int J. Pharm vol. 17, p. 135.

Van Bommel, et al., Stability of Doxorubicin–Liposomes on Storage as an Aqueous Dispersion, Frozen or Freeze dried (1984), Int J Pharm, vol. 22, pp. 299–310.

Crommelin et al., Preparation and characterization of doxorubicin–containing lipsomes. I Influence of liposome charge and pH of hydration medium on loading capacity and particle size, (1983), Int. J Pharm., vol. 16, pp. 93–96.

Gupta et al., "Influence of Stabilization Temperature on the Entrapment of Adriamycin", *Albumin Microspheres Drug. Dev. Int. Pharm.*, vol. 13, No. 8, pp. 1471–1482, (1987).

Yanagawa et al. Stability and Releasibility of Adriamycin Ointment (1983).

Vilallonga et al. Interaction of Doxorubican with Phospholipid Monolayers, J Pharm Sci. 67(6). p. 773 (1978).

Duarte–Karim et al., Affinity of adriamycin to phospholipids. A possible explanation for cardiac mirochonorial lesions, (1976) Biochem Biophy. Research Comm., 71(2), p. 658.

Bonadonna et al, Clinical Evaluation of Adriamycin a New Antitumor Antibiotic, Br. Med J., (3), 503 (Aug. 1969).

Banks et al., Topical Installation of Doxorubicin Hydrochloride in the Treatment of Recurring Superficial Transitional Cell Carinoma of the Bladder, J. Ulrol., vol. 118, p. 757 (1977).

Bertazzoli et al, Chronic toxicity of adriamycin a new antineoplastic antibiotic (1972). Tox Applied Pharm, vol. 2, pp. 287–301.

Wang et al., Therapeutic effect and toxicity of adriamycin in patients with neoplastic disease. (1971) Cancer. 28, p. 837.

Horn et al., Intravesical chemotherapy in a controlled trial with thio–tepa versus doxorubicin hydrochloride (1981) J. Urol., 125–652.

Jacobi et al., Studies on the intravesical action of topically administered G3H–doxorubicin hydrochloride in men: plasma uptake and tumor penetration (1980). J Urol. 123:34.

Jaenke, R S.: Delayed and progressive myocardial lesions after adriamycin administration in the rabbit (1976) Cancer Res. vol. 36, pp. 2958–2966.

Casazza et al., Tumors and dental ocular abnormalities after treatment of infant rats with adriamycin. (1977) Tumor 63:331.

Barranco et al, Survival and cell kinetics effects of adriamycin on mammalian cells, (1973) Cancer Res 33:11.

Gaj et al., Evaluation of growth in Five Microorganisms in Doxorubicin and Floxuridine Media, (1984) Pharm. Manuf., p. 50.

Sturgeon and Schulman: Electronic Absorption Spectra and Protolytic Equlibria of Doxorubicin: Direct Spectrophotometric Determination of Microconstants, J Pharm. Sci. 66(7) 958, (1977).

Dalmark et al, A Fickian Diffusion Transport Process with Features of Transport Catalysis. J. Gen Physiol. 78:349 (1981).

Masuike et al, Determination of Adriamycin and its Metabolites in Biological samples using high performance liquid chromatography Chemical Abstracts (1984), vol. 101, p. 5.

Barth et al., "Determination of Doxorubicin Hydrochloride.", *Pharmaceutical Preparations using High Pressure Liquid Chromatography*, (1977) J. of Chromatography vol. 131, p. 375–381.

Arena et al., Analysis of the pharmacokinetic characteristics, pharmacological and chemotherapeutic activity of 14–hydroxy–daunomycin (adriamycin), a new drug endowed with an Antitumor activity, (1971) Drug Res. 21: 1258.

Watson et al., Rapid analytic method for adriamycin and metabolites in human plasma by a thin film flourescence scanner (1976) Cancer Treat. Rep., vol. 60, No. 11, p. 1611.

Langone et al., Adriamycin and Metabolites: Separation by High Pressure Liquid Chromatography and Qunitation by Radioimmunossay, Biochem Med. 12:283 (1975).

Benjamin et al., Pharmacokinetics and metabolism of adriamycin in man, Clin. Pharm. Ther, 14(4) Part 1, 592.

Epirubicin, Drugs of the Future, vol. 8,(5): p. 402, (1985).

Cersosimo et al., Epirubicin: A Review of the Pharmacology, Clinical Activity, and Adverse Effects of an Adriamycin Analogue, J Clin Oncol 4(3), 425 (1986).

Fischer, "The Cancer Chemotherapy Handbook", $3^{rd}$ Edition, (1989). pp. 87–89.

De Vroe, et. al., A Study on the stability of three antineoplastic drugs and on their sorption by iv delivery systems and end–line filters, (1990). Int. J. Pharm. vol. 65, pp. 49–56.

DeVries, et. al., A Phase I and Pharmocokinetic Study with 21 day Continuous infusion of Epirubicin, J. Clin. Oncol., (1987), 5(9), 1445–1451.

Adams, et. al. Pharmaceutical Apsects of Home Infusion Therapy for Cancer Patients. (Apr. 1987). Pharm. J., p. 476.

Weenen, et al., "Pharmacokinetics of 4–Epi–doxorubicin in Man", Invest. New Drugs, vol. 1, (1983), p. 59.

Arcamone, et. al., "Synthesis and Antitumor Activity of 4–Demethoxydaunorubicin, 4–Demothoxy–9–diepidaunorubicin, and their beta anomers", Cancer Treat Rep. 60(7):829 (1976).

Turowski et al., "Visual Compatability of Idarubicin Hydrochloride with selected drugs during simulated Y–site injection", (Oct. 1991), Ans. J. Hosp. Pharm., vol. 48, p. 2181.

Hurteloup et al., Phase II Trial of Idarubicin (4–Demethoxydaunorubicin) in Advanced Breast Cancer. Eur. J. Cancer Clin. Oncol. 25(3)432 (1989).

Kaplan et al., Phase I Trial of 4–Demethoxydaunoribicin with single i.v. doses, Eur J Clin Cancer Oncol., 18(12) 1303 (1982).

Reich et al., "Carminomycin", *Arptheacyclines: Current Status and New Developments*, (1980) (J. Cooke et al., eds.) Academic Press, p. 295.

Brazhnikova et al., "Physical and Chemical Characteristics and Structure of Carminomycin, a New Antitumour Antibiotic", J. Antibiot, 27(4):254 (1974).

Brazhnikova et al., "Carminomycin, a New Antitumor Anthracycline" (1973) Antibiotiki 18:681.

Crooke, "A Review of Carminomycin, A New Anthracycline Developed in the USSR" J. Med. 8(5) 295 (1977).

Lankelma et al, "Plasma Concentrations of Carminomycin and Carminomycinol in Man. Measured in High Pressure Liquid Chromatography", Eur. J. Cancer clin. Oncol. 18(4):363 (1982).

Fandrich, "Analysis of Carminomycin in Human Serum by Fluorometric High–Performance Liquid Chromatography", J Chromatogr. 223 155 (1981).

Oki, "Aclacinomycin A Anthracyclines: Current Status and New Developments", (1980) Academic Press., p. 323.

Oki et al., "Antitumor Anthracycline Antibiotics, Aclacinomycin A and Analogues: I. Taxonomy, Production, Isolation and Physicochemical Properties", J. Antibiot 32(8):791 (1979).

Oki, "New Antitumor Antibiotics, Aclacinomycins A and B", J. Antibiot, 28(10) 830 (1975).

Mori et al., "Physicochemical Properties and Stability of Aclacinomycin A Hydrochloride," (1980) Jpn. J. Antiboit 33 618.

Trissel, "Handbook on Injectable Drugs", $5^{th}$ Edition, p. 707.

Fischer, "The Cancer Chemotheraphy Handbook", $3^{rd}$ Edition, pp. 17–19.

Arcamone et al, "Synthesis and Antitumor Activity of 4–Deoxydaunorubicin and 4–Deoxyadriamycin", J. Med. Chem. 19(12).1424 (1976).

Fischer, "The Cancer Chemotherapy Handbook" $3^{rd}$ Edition (1989), p. 88.

Salmon et al, "Antitumour Activity of Esorubicin in Human Tumour Clonogenic Assay with Comparison to Doxorubicin", J. Clin. Oncol 2(4):282 (1984).

Kovach et al. "Phase I Trial & Assay of Rubidozone (NSC 164011) in Patients with Advanced Solid Tumors", (Mar. 1979) Cancer Research vol. 39, p. 823.

Deprez–de Campanere et al. "Pharmacokinetic, Toxicologic, and Chemotherapeutic Properties of Detorubicin in Mice: A Comparative Study with Daunourubicin and Adriamycin", Cancer Treat Res. 63(5):861 (1979).

Bono, "The Preclinical Development of Quelamycin and its Initial Clinical Trials", *Anthracyclines: Current Status and New Developments*, (1980) Academic Press, p. 315.

Gosalvez et al. "Quelamycin, a New Derivative of Adriamycin with Several Possible Therapeutic Advantages", Eur. J. Cancer 14.1185 (1978).

Reich et al, "Marcellomycin" *Anthracylcines Current Status and New Developments*, (1980) Academic Press, p. 343.

Nettleston et al., New Antitumour Antibiotics: Musettamycin and Marcellomycin from Bohemic Acid Complex: (1977) 30(6) J. Antibiotics 525.

Israel et al., "Adriamycin Analogues Preparation and Biological Evaulation of Some N–Perfluoracyl Analogues of Daunorubicin, Adriamycin, and N–(trifluoroacetyl) adriamycin 14–valerate and their 9, 10–Anhydro Derivatives" J Med Chem 25 187 (1982).

Tong et al., "5–Iminodaunorubicin: Reduced Cardiotoxic Properties in an Antitumour Anthracycline". J. Med. Chem 22(1): 36 (1979).

Arcamone et al., "Synthesis and Antitumour Activity of new Daunorubicin and Adriamycin Analogues" (1978) Experientia 34:1255.

Umezawa et al., "Tetrahydropyranly Derivatives of Daunomycin and Adriamycin", J. Antibiol 32(10):1082 (1979).

Chen et al., "Possible Strategies for the Formulation of Antineoplastic Drugs" (1986) Drug Dev Ind Pharm vol. 12(7) 1041.

Pharmaceutics—The science of dosage form design (Aulton) (1988). pp. 242–244, 252–253, 368–369, 374–375, 380–.

Experimental Pharmaceutical Technology, $2^{nd}$ Ed.(Parrott & Saski). 1965, pp. 132–134, 149–154.

Pharmaceutics & Pharmacy Practice (1982) (Banker & Chalmers), pp. 238–243, 275–278.

Pharmaceutical Dosage Forms. Parenteral Medications: vol. 1 (Avis et al. 1984) "Biopharmaceutics of Injectable Medication" (Motola).

Connors et al, "Chemical Stability of Pharmaceuticals—a Handbook for Pharmacists" (1979) Wiley. pp. 3–7, 44–63, 74–75.

Ozturk et al., "Dissolution of Ionizable Drugs in Buffered and Unbuffered Solutions" (1988) 5(5) Pharm. Res 272.

Gordon et al., "The Art and Science of Contemporary Drug Development", Prog. Drug. Res. 16:194 (1972).

Pharmaceutical Dosage Forms: Parenteral Medications: vol. 1 (Avis et al. 1984), "Preformulation Research of Parenteral Medications" (Motola & Agharkar).

The Theory & Practice of Industrial Pharmacy (Lachman et al.), $3^{rd}$ Ed. 1986, p. 191, et seq., pp. 191–194, 195–196, 459–460, 471–472, 477–478, 764–765.

Lin, "Kinetic Study in Formulation Investigation of New Compounds" (1968).

Zoglio, "Preformulation Stability Testing of Parenteral Products" (1968).

Knoop, "The Pharmaceutical Drug Development Process: An Overview" (1988) 22 Drug Inf. J 259.

Rees, "Physico–Mechanical Pre–Formulation Studies" (1973) 112 Boll. Chim. Farm. 216.

Monkhouse, "Dosage Forms For Clinical Trials" (1985) 11 (9 & 10) Drug Dev. Ind. Pharm. 1729.

Graffner et al., "Preformulation Studies in a Drug Development Program for Tablet Formulations". J Pharm. Sci. 74(1) 16 (1985).

Davignon et al., Pharmaceutical Aspects of Antitumor Agents (1984) Pharm. Weekbr 119 1144.

Pharmaceutical Dosage Forms: Parenteral Medications vol. 2 (Avis et al., 1984) "Formulations for Large Volume Parenterals" (Demorest). pp. 55–63, 68–70, 73–76, 83.

Pharmaceutical Dosage Forms: Parenteral Medications: vol. I(Avis et al., 1984) "Formulation for Small Volume Parenterals" (DeLuca & Boylan).

Schumacher (ed), Bulk Compounding Technology.

Carlin, "Incompatibilities of Parenteral Medications" (Jun. 1968) 25 Am J Hosp. Pharm. 271.

Kalmas, et al., "Solubility Aspects in Parenteral Formulation" (May/Jun. 1982) Ind. J. Hosp. Pharm. 94, pp. 94–96, 98, Table I.

Parrott, Formulation of Parenterals.

Lin, "Parenteral Formulations I. Comparisons of Accelerated Stability Data with Shelf–Life Studies". Bull. Par. Drug Assoc. 23(6):269.

Lin, "Parenteral Formulations II. A Stability Testing Program for Parenteral Products", Bull Par. Drug Assoc 24(2).83.

Lin, "Photochemical Considerations of Parenteral Products", Bull. Par. Drug Assoc 23 (4):149.

National Coordinating Committee on Large Volume Parenterals, "Recommendations to Pharmacists for Solving Problems with Large–Volume Parenterals", Am. J Hosp. Pharm. 33.231 (1976).

Zellmer, "Solving Problems with Large–Volume Parenterals, 1: Pharmacist Responsibility for Compounding Intravenous Admixtures", Am. J. Hosp. Pharm. 32.255 (1975).

Pharmaceutical Dosage Forms, "Parenteral Medications: vol. 1 (Avis et al. 1984)—Parenteral Drug Administration: Routes, Precautions, Problems & Complications" (Duma & Akers).

Edward, "pH: An important Factor in the Compatibility of Additives In Intravenous Therapy" (Aug. 1967) vol. 24 Am. J. Hosp Pharm. 440.

Document entitled "Kinetic pH Profiles", pp. 59–121, 380–385.

Remington's Pharmaceutical Sciences, $18^{th}$ ed. 1990. ch. 17 Ionic Solutions & Electrolytic Equilibris.

Advances in Pharmaceutical Services, vol. 2 (Bean et al., 1967), pp. 62–75, 80–95.

Fynn, "Buffers–pH Control within Pharmaceutical Systems" (Mar.–Apr. 1980) vol. 34(2) J. Parenteral Drug Assoc. 139.

Windheuser, "The Effect of Buffers on Parenteral Solutions" (Sep. Oct. 1963) vol. 17(5) Bull Parenteral Drug Assoc.

Rubino, "The Effects of Cosolvents on the Action of Pharmaceutical Buffers" (1987) 41(2) J. Paren Sci Tech 45.

Kramer & Flynn, "Solubility of Organic Hydrochlorides" (Dec. 1972) vol. 61 (12) J. Pharm Sci. 1896.

Tencheva et al., "New Approach of the Extrapolation Procedure in the Determination of Acid–Base Constants of Poorly Soluble Pharmaceuticals" (1979), Arzneim Forsch/Drug Res. 29 (II)=9.

Bogardus et al., "Solubility of Doxycylcine in Aqueous Solutions" (Feb. 1979) vol. 68 (2) J. Pharm Sci 188.

Miyazkai et al., "Precaution of Use of Hydrochloride Salts in Pharmaceutical Formulation" (Jun. 1981) 70(6) J. Pharm. Sci. 594.

Greene et al., Stability of cicplatin in aqueous solution. Am J Hosp. Pharm. 36:3S (1979).

Stjernstrom et al: Studies on the stability and compatibility of drugs in infusion fluids. Acta Pharm Spec. 15.33 (1978).

Ho Prediction of Pharmaceutical Stability of Parenteral Solutions III (Feb. 1971) vol. 5. Drug. Int Clin. Pharm 47.

Stella: Chemical and Physical Bases Determining the Instability and Incompatibility of Formulated Injectable Drugs (1986) 40(4) J. Paren. Sci. Tech. 142.

Newton. "Physicochemical Determinants of Incompatibility and Instability in Injectable Drug Solutions and Admixtures" (1978) 35 Am. J. Hosp. Pharm. 1213.

Mendenhall: Stability of Parenterals (1984) Drugs Dev. Ind. Pharm. 10(8–9) 1297.

Singh et al.: Effect of Solvents and Additives on the Stability of Drugs, Pharma Times 13.

Pope: Accelerated Stability Testing for Prediction of Drug Product Stability—First of a Two–Part Article (Nov., 1980) D & CI 54, pp. 54, 56, 59, 60, 62, 116.

Pope: Accelerated Stability Testing for Prediction of Drug Product Stability—Second of a Two–Part Article (Dec., 1980) D & CI 48, pp. 48, 50, 55, 56, 58, 60, 62, 64–66, 110, 112–116.

Amirjahed: Simplified Method to Study Stability of Pharmaceutical Preparations, J. Pharm Sci pp(6).785 (1977).

Vogenberg et al., Stability Guidelines for Routinely Refrigerated Drug Products, Am. J. Hosp Pharm. 40:101(1983).

Newton et al. Estimating shelf–life of drugs in solution. Am. J Hosp Pharm 44:1633 (1987).

Mollica et al., Stability of Pharmaceuticals. J Pharm Sci 67(4).443 (1978).

King et al Statistical Prediction of Drug Stability Based on Non–Linear Parameter Extension. J Pharm Sci. 73(5):657.

Herrick et al.: Monetary incentive for pharmacists to control drug costs; (Jul 1985) vol. 42. Am. J Hosp Pharm 1527.

Waller: Documenting i.v. admixture product waste (Aug. 1980) vol. 43, Am J Hosp. Pharm 1914.

Williams et al., The Lyophilization of Pharmaceuticals: A Literature Review (1984) 38(2) J Paren Sci. Tech 48.

Flamberg et al.: Manufacturing Considerations in the Lyophilization of Parenteral Products (1986) Pharm. Manuf 3:29–31.

Maral et al Un Nouvel Antibiotique Doue D'Activite Antitumorale: La Rubidomycine (13 057 R P). II: Activate antitumorale experimentale Arzncimittel Forsch (1967) 17 939.

Beijnen et al.: Aspects of the Degradation Kinetics of Doxorubicin in Aqueous Solution (1986) 32 Int J. Pharm 123.

Gjelstrup et al., Almen Farmaci II (1983).

Handbook on Injectible Drugs $3^{rd}$ Ed. (Trissel), 1983.

Wang et al, "Review of Excipients and pH's for Parenteral Products Used in the United States", Journal of the Parenteral Drug Association 14(6).452 (1980).

Jonkman–de Vries et al., "Pharmaceutical Development of a Parental Lyophilized Formulation of the Novel Indoloquinone Antitumor Agent EO", Cancer Chemother. Pharmacol 34.416–422 (1994).

Pharmaceutical Sciences, Mack Publishing, (1980), pp. 1365–1366.

The Pharmaceutical Codex $11^{th}$ Ed., 1979, pp. 446–447.

The Pharmaceutical Codex $12^{th}$ Ed. (Lund), 1994, p. 201.

Kjeld Ilver: Almen Galenisk Farmaci—Forel≧sningsnoter, Dansk Farmaceutforenings Forlag 1971.

Sv. Aage Schou & V. Gaun Jensen: Tr≧k af den glaeniske farmaci, Store Nordiske Videnskabsboghandel, 1959.

Almen Farmaci. Dansk Farmaceutforenings Forlag 1980.

Erik Sandell: Galenisk Farmaci, $2^{nd}$ edition, Stockholm 1967.

Erik Sandell: Galenisk Farmaci, $3^{rd}$ edition, Stockholm 1982.

User information for ADRIBLASTIN®, Apr. 1983.

Alfred N. Martin et al., PHysikalische Pharmazie 1975, p. 239.

European Pharmacopeia, vol. III, 1979, p. 656 Citations—D 14.

Bradner and Misiek, (1977) The Journal of Antibiotics, "Bohemic Acid Complex Biological Characterization of the Antibiotics. Musettamycin and Marcellomycin," 30(6) 519–522.

Kjeld Ilver, Almen Galenisk Farmaci—Forelæsningsnoter, Dansk Farmaceutforenings Forlag 1971, pp. 132–136 (English translation provided).

Gjelstrup et al. (1983). Almen Farmaaci I. Dansk Farmaceutforenings Forlag, København. pp. 404–408, 440, 442–443, 447, 451 (English translation provided).

Erik Sandell, (1967), Galenisk Farmaci, $2^{nd}$ edition, Stockholm, p. 214 (English translation provided).

Erik Sandell, (1982), Galenisk Farmaci, $3^{rd}$ edition, Stockholm, p. 123 (English translation provided).

Svend Aage Schou & V. Gauneø Jensen (1959), Træk af den flaeniske farmaci, Store Nordiske Videnskabsboghandel, p. 220. (English translation provided).

Arcomone, F. (1977). Lloydia, "New Antitumor Anthracyclines." 40(1):45–66.

Naff et al., (1982) Anthracycline Antibiotics, Anthracyclines in the National Cancer Institute Program. Hassan S. El Khadam, editor, Academic Press, pp. 1–57.

Formularium Der Nederlandse Apothekers, (1983) pp. 18, 124, 133.

Formularium Der Nederlandse Apothekers, (1979) pp. 1.64, 1.82.

Formularium Der Nederlandse Apothekers, (1985) p. 1.64a.

Formularium Der Nederlandse Apothekers, (1989) p. 1.88.

Formularium Der Nederlandse Apothekers, (1992) p. 1.63a.

Bohme and Harke (1979), Europäisches Arzneibuch,Band III, Kommentar, Wissenschaftliche Verlagsgesellschaft mbH Stuggart, p. 654 (English translation provided).

Arcamone et al (1972), "Structure and Physicochemical Properties of Adnamycin (Doxorubicin)," International Symposium on Adriamycin, pp. 9–22.

Wang and Kowal (1980), "Review of Excipients and pH's for Parenteral Products Used in the United States," Journal of the Parenteral Drug Association, pp. 452–462.

Harns, Quantitative Chemical Analysis, Fourth Edition, W.H. Freeman & Company, New York, p. 240.

Bernard et al., editors (1969), Rubidomycin A New Agent Against Cancer, pp. ix–181.

Kansen et al. (1983), "Stability of cytotixic intravenous solutions subjected to freeze–thaw treatment," Nor. Pharm. Acta, 45, 61–67.

INJECTABLE READY-TO-USE SOLUTIONS CONTAINING AN ANTITUMOR ANTHRACYCLINE GLYCOSIDE

This is a continuation application of U.S. application Ser. No. 07/827,742, filed Jan. 29, 1992 now U.S. Pat. No. 6,107,285, which is a divisional application of U.S. Ser. No. 07/503,856, filed Apr. 3, 1990 now U.S. Pat. No. 5,124,317 which is a divisional application of U.S. Ser. No. 07/385,999, filed Jul. 27, 1989 now U.S. Pat. No. 4,946,831 which in turn is a continuation application of U.S. Ser. No. 878,784, filed Jun. 26, 1986, now abandoned.

The present invention relates to a stable intravenously injectable ready-to-use solution of an antitumor anthracycline glycoside, e.g. doxorubicin, to a process for preparing such a solution, and provide the same in a sealed container, and to a method for treating tumors by the use of the said ready-to-use solution.

The anthracycline glycoside compounds are a well known class of compounds in the antineoplastic group of agents, wherein doxorubicin is a typical, and the most widely used, representative: Doxorubicin. Anticancer Antibiotics, Federico Arcamone, 1981, Publ: Academic Press, New York, N.Y.; Adriamycin Review, EROTC International Symposium, Brussels, May, 1974, edited by M. Staquet. Publ. Eur. Press Medikon, Ghent, Belg.;

Results of Adriamycin Therapy, Adriamycin Symposium at Frankfurt/Main 1974 edited by M. Ghione, J. Fetzer and H. Maier, publ.: Springer, New York, N.Y.

At present, anthracycline glycoside antitumor drugs, in particular, e.g., doxorubicin, are solely available in the form of lyophilized preparations, which need to be reconstituted before administration.

Both the manufacturing and the reconstitution of such preparations expose the involved personnel (workers, pharmacists, medical personnel, nurses) to risks of contamination which are particularly serious due to the toxicity of the antitumor substances.

The Martindale Extra Pharmacopoeia 28th edition, page 175 left column, reports, indeed, about adverse effects of antineoplastic drugs and recommends that "They must be handled with great care and contact with skin and eyes avoided; they should not be inhaled. Care must be taken to avoid extravasation since pain and tissue damage may ensue."

Similarly, Scand. J. Work Environ Health vol. 10 (2), pages 71–74 (1984), as well as articles on Chemistry Industry, Issue Jul. 4, 1983, page 488, and Drug-Topics-Medical-Economics-Co, Issue Feb. 7, 1983, page 99 report about severe adverse effects observed in medical personnel exposed to use of cytostatic agents, including doxorubicin.

To administer a lyophilized preparation, double handling of the drug is required, the lyophilized cake having to be first reconstituted and then administered and, moreover, in some cases, the complete dissolution of the powder may require prolonged shaking because of solubilization problems.

As the risks connected with the manufacturing and the reconstitution of a lyophilized preparate would be highly reduced if a ready-to-use solution of the drug were available, we have developed a stable, therapeutically acceptable intravenously injectable solution of an anthracycline glycoside drug, e.g. doxorubicin, whose preparation and administration does not require either lyophilization or reconstitution.

According to the present invention, there is provided a sterile, pyrogen-free, anthracycline glycoside solution which consists essentially of a physiologically acceptable salt of an anthracycline glycoside dissolved in a physiologically acceptable solvent therefor, which has not been reconstituted from a lyophilizate and which has a pH of from 2.5 to 6.5.

Preferably the solution of the invention is provided in a sealed container.

Preferably the anthracycline glycoside is chosen from the group consisting of doxorubicin, 4'-epi-doxorubicin (i.e. epirubicin), 4'-desoxy-doxorubicin (i.e. esorubicin), 4'-desoxy-4'-iodo-doxorubicin, daunorubicin and 4-demethoxydaunorubicin (i.e. idarubicin).

A particularly preferred anthracycline glycoside is doxorubicin.

Any physiologically acceptable salt of the anthracycline glycoside may be used for preparing the solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutammic, benzoic, methanesulfonic, ethanesulfonic and the like. The salt with hydrochloric acid is a particularly preferred salt, especially when the anthracycline glycoside is doxorubicin.

Any solvent which is physiologically acceptable and which is able to dissolve the anthracycline glycoside salt may be used. The solution of the invention may also contain one or more additional components such as a co-solubilizing agent (which may be the same as a solvent), a tonicity adjustment agent and a preservative. Examples of solvents, co-solubilizing agents, tonicity adjustment agents and preservatives which can be used for the preparation of the anthracycline glycoside solutions of the invention are hereunder reported.

Suitable solvents and co-solubilizing agents may be, for instance, water; physiological saline; aliphatic amides, e.g. N,N-dimethylacetamide, N-hydroxy-2-ethyl-lactamide and the like; alcohols, e.g. ethanol, benzyl alcohol and the like; glycols and polyalcohols, e.g. propyleneglycol, glycerin and the like; esters of polyalcohols, e.g. diacetine, triacetine and the like; polyglycols and polyethers, e.g. polyethyleneglycol 400, propyleneglycol methylethers and the like; dioxolanes, e.g. isopropylidenglycerin and the like; dimethylisosorbide; pyrrolidone derivatives, e.g. 2-pyrrolidone, N-methyl-2-pyrrolidone, polyvinylpyrrolidone (co-solubilizing agent only) and the like; polyoxyethylenated fatty alcohols, e.g. Brij$^R$ and the like; esters of polyoxyethylenated fatty acids, e.g. Cremophor$^R$, Myrj$^R$ and the like; polysorbates, e.g. Tweens$^R$; polyoxyethylene derivatives of polypropyleneglycols, e.g. Pluronics$^R$.

A particularly preferred co-solubilizing agent is polyvinylpyrrolidone.

Suitable tonicity adjustment agents may be, for instance, physiologically acceptable inorganic chlorides, e.g. sodium chloride, dextrose, lactose, mannitol and the like.

Preservatives suitable for physiological administration may be, for instance, esters of para-hydroxybenzoic acid (e.g., methyl, ethyl, propyl and butyl esters, or mixtures of them), chlorocresol and the like.

The above mentioned solvents and co-solubilizing agents, tonicity adjustment agents and preservatives can be used alone or as a mixture of two or more of them.

Examples of preferred solvents are water, ethanol, polyethyleneglycol and dimethylacetamide as well as mixtures in various proportions of these solvents. Water is a particularly preferred solvent.

To adjust the pH within the range of from 2.5 to about 5.0 a physiologically acceptable acid may be added as desired. The acid may be any physiologically acceptable acid, e.g., an inorganic mineral acid such as hydrochloric, hydrobromic, sulfuric, phosphoric, nitric and the like, or an organic acid such as acetic, succinic, tartaric, ascorbic, citric, glutammic, benzoic, methanesulphonic, ethanesulfonic and the like, or also an acidic physiologically acceptable buffer solution, e.g., a chloride buffer, an acetate buffer, a phosphate buffer and the like.

For obtaining pH values from about 5 to about 5.5 the addition of the acid is not, usually, necessary, but only addition of a physiologically acceptable buffer solution, e.g., one of those indicated above, may be required, as desired.

For obtaining pH values from about 5.5 to 6.5 the addition of a physiologically acceptable alkalinizing agent, such as sodium hydroxide, a mono, di- or triethanolamine or the like, or, preferably, a buffer solution such as a phosphate buffer, a TRIS buffer or the like is required.

The preferred range of pH for the ready-to-use solution of the invention is from 2.5 to 5.5, in particular from about 3 to about 5.2, a pH of about 3 and a pH of about 5 being particularly preferred values.

In the solutions of the invention the concentration of the anthracycline glycoside may vary within broad ranges, preferably from 0.1 mg/ml to 100 mg/ml, in particular from 0.1 mg/ml to 50 mg/ml, most preferably from 1 mg/ml to 20 mg/ml.

The preferred ranges of concentration may be slightly different for different anthracycline glycosides. Thus, for example, preferred concentrations for doxorubicin are from about 2 mg/ml to about 50 mg/ml, preferably from 2 mg/ml to 20 mg/ml, particularly appropriate values being 2 mg/ml and 5 mg/ml. Similar concentrations are preferred also for 4'-epi-doxorubicin, 4'-desoxy-doxorubicin and 4'-desoxy-4'-iodo-doxorubicin. Preferred ranges of concentration for daunorubicin and 4-demethoxy-daunorubicin are from 0.1 mg/ml to 50 mg/ml, preferably from 1 mg/ml to 20 mg/ml, concentrations of 1 mg/ml and 5 mg/ml being particularly appropriate.

Suitable packaging for the anthracycline glycoside solutions may be all approved containers intended for parenteral use, such as plastic and glass containers, ready-to-use syringes and the like. Preferably the container is a sealed glass container, e.g. a vial or an ampoule.

According to a particularly preferred feature of the invention, there is provided a sterile, pyrogen-free, doxorubicin solution which consists essentially of a physiologically acceptable salt of doxorubicin dissolved in a physiologically acceptable solvent therefor, which has not been reconstituted from a lyophilizate and which has a pH of from 2.5 to 6.5.

In the above indicated preferred feature of the invention the physiologically acceptable salt of doxorubicin may be, e.g. the salt with a mineral inorganic acid such as hydrochloric, hydrobromic, sulfuric, phosphoric, nitric and the like, or the salt with an organic acid such as acetic, succinic, tartaric, ascorbic, citric, glutammic, benzoic, methanesulfonic, ethanesulfonic and the like. The hydrochloride salt is a particularly preferred salt.

For the solution hereabove indicated as a preferred feature of the invention suitable solvents, co-solubilizing agents, tonicity adjustment agents and preservatives may be the same as those previously recited in the specification. Water is a particularly preferred solvent.

Also, the physiologically acceptable acid which may be added to adjust the pH to from 2.5 to about 5, if desired, and the alkanilizing agent which may be added to adjust the pH, if desired, to a value from about 5.5 to 6.5 may be one of those previously specified. When it is desired to adjust the pH of the above said preferred solution to a value of from 2.5 to about 5, hydrochloric acid is an especially preferred acid.

Preferred pH values for the above said preferred solutions of the invention are from 2.5 to 5.5, in particular from about 3 to about 5.2, the pH values of 3 and 5 being especially preferred.

Though the concentration of doxorubicin in the above preferred feature may vary within the broad range from 0.1 mg/ml to 100 mg/ml, preferred concentrations are from 2 mg/ml to 50 mg/ml, most preferably from 2 mg/ml to 20 mg/ml: examples of especially preferred concentrations of doxorubicin are 2 mg/ml and 5 mg/ml.

The invention also provides a process for producing a sterile, pyrogen-free anthracycline glycoside solution with a pH of from 2.5 to 6.5, which process comprises dissolving a physiologically acceptable salt of the anthracycline glycoside, which salt is not in the form of a lyophilizate, in a physiologically acceptable solvent therefor; optionally adding a physiologically acceptable acid or buffer to adjust the pH within the said range as desired; and passing the resulting solution through a sterilising filter.

One or more additional components such as co-solubilizing agents, tonicity adjustment agents and preservatives, for instance of the kind previously specified, may be added to the solution prior to passing the solution through the sterilising filter.

With the solutions of the invention it is possible to obtain compositions having a very high concentration of the anthracycline glycoside active substance even at 50 mg/ml and more. This constitutes a great advantage over the presently available lyophilized preparates wherein high concentrations of anthracycline glycoside can only be obtained with difficulty because of solubilization problems encountered in reconstitution, mainly with saline. The presence of the excipient, e.g. lactose, in the lyophilized cake, and its generally high proportion in respect of the active substance, even up to 5 parts of excipient per part of active substance, has a negative effect on solubilization so that difficulties may arise in obtaining dissolution of the lyophilized cake, especially for concentrations of anthracycline glycoside higher than 2 mg/ml.

The solutions of the invention are characterized by a good stability. Solutions in various solvents and with different pH's and concentrations have been found to be stable for long periods at temperatures accepted for the storage of pharmaceutical preparations. This is illustrated in the Examples which follow.

Owing to the well known anti-tumor activity of the anthracycline glycoside active drug substance, the pharmaceutical compositions of the invention are useful for treating tumors in both human and animal hosts. Examples of tumors that can be treated are, for instance, sarcomas, including osteogenic and soft tissue sarcomas, carcinomas, e.g., breast-, lung-, bladder-, thyroid-, prostate- and ovarian carcinoma, lymphomas, including Hodgkin and non-Hodgkin lymphomas, neuroblastoma, melanoma, myeloma, Wilms tumor, and leukemias, including acute lymphoblastic leukemia and acute myeloblastic leukemia.

Examples of specific tumours that can be treated are Moloney Sarcoma Virus, Sarcoma 180 Ascites, solid Sarcoma 180, gross transplantable leukemia, L 1210 leukemia and lymphocytic P 368 leukemia.

Thus, according to the invention there is also provided a method of inhibiting the growth of a tumour, in particular one of those indicated above, which comprises administering to a host suffering from said tumour an injectable solution according to the invention containing the active drug substance in an amount sufficient to inhibit the growth of said tumour.

The injectable solutions of the invention are administered by rapid intravenous injection or infusion according to a variety of possible dose schedules. Suitable dose schedule for doxorubicin may be, for example, of 60 to 75 mg of active drug substance per m² of body surface given as a single rapid infusion and repeated at 21 days; an alternative schedule may be of 30 mg/m² day by intravenous route for 3 days, every 25 days. Suitable dosages for 4'-epi-doxorubicin and 4'-desoxy-doxorubicin may be, for instance, of 75 to 90 mg/m² given in a single infusion to be repeated at 21 days, and similar dosages may be useful for 4'-desoxy-4'-iodo-doxorubicin.

Idarubicin, i.e. 4-demethoxy-daunorubicin, may be, e.g., administered intravenously at a single dose of 13–15 mg/m² every 21 days in the treatment of solid tumours, while in the treatment of leukemias a preferred dose schedule is, e.g., of 10–12 mg/m² day by intravenous route for 3 days, to be repeated every 15–21 days; similar dosages may be, e.g., followed also for daunorubicin.

The following examples illustrate but do not limit in any way the invention.

With reference to the examples, the stability controls on the ready-to-use solutions were carried out by means of high performance liquid chromatography (HPLC), at the following experimental conditions:

| | |
|---|---|
| Liquid chromatograph | Varian model 5010 |
| Spectrophotometric detector | Knauer model 8700 |
| Integrating recorder | Varian model CDS 401 |
| Injection valve | Rheodyne model 7125 fitted with a 10 mcl sample loop |
| Chromatographic column | Waters µ-Bondapak C18 (length = 300 mm; inner diameter = 3.9 mm; average particle size = 10 mcm) |
| Column temperature | ambient (about 22° C. ± 2° C.) |
| Mobile phase | water:acetonitrile (69:31 v/v) adjusted to pH 2 with phosphoric acid, filtered (sintered glass filter, 1 mcm or finer porosity) and deaerated |
| Mobile phase flow rate | 1.5 ml/min |
| Analytical wavelength | 254 ± nm |
| Integrating recorder sensitivity | 512 |
| Chart speed | 1 cm/min |

At these conditions, the peak of the anthracycline glycoside showed a retention time of about 6 minutes.

The obtained results are reported in the Tables accompanying the examples.

The extrapolation of the analytical data in order to determine the time when the 90% of the initial assay could be expected ($t_{90}$ value) was made following an Arrhenius plot.

This procedure of analytical data treatment is well known and widely used and described in the art: see, e.g., Chemical Stability of Pharmaceuticals, Kennet A. Connors, Gordon L. Amidon, Lloyd Kennon, Publ. John Wiley and Sons, New York, N.Y., 1979.

The term "teflon" refers to "Teflon™".

EXAMPLE 1

| Composition | for 80 vials | (for 1 vial) |
|---|---|---|
| Doxorubicin.HCl | 0.8 g | (10 mg) |
| Water for injections q.s. to | 0.4 l | (5 ml) |

Doxorubicin.HCl (0.80 g) was dissolved in 90 percent of the amount of water for injections, de-aerated by nitrogen bubbling. The pH of the solution was not adjusted. Further de-aerated water for injections was then added to bring the solution to its final volume (0.40 l).

The solution was filtered through a 0.22µ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 1:

TABLE 1

INITIAL VALUES

Concentration: 1.994 mg/ml
Relative % Assay: 100.0   pH = 5.2

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % As-say | Conc. mg/ml | Rel. % As-say | Conc. mg/ml | Rel. % As-say | Conc. mg/ml | Rel. % As-say |
| 1 | 1.992 | 99.9 | 1.917 | 96.1 | 1.768 | 88.7 | 1.493 | 75.0 |
| 2 | | | 1.843 | 92.4 | 1.618 | 81.1 | 1.166 | 58.5 |
| 3 | | | 1.774 | 89.0 | 1.506 | 75.5 | 0.830 | 41.6 |
| 4 | 1.974 | 99.0 | 1.720 | 86.3 | 1.393 | 69.9 | | |
| 12 | 1.980 | 99.3 | | | | | | |

$t_{90}$ (days) extrapolated according to Arrhenius equation:
$t_{90}$ at 4° C. = 815 days
$t_{90}$ at 8° C. = 480 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 2

| Composition | for 80 vials | (for 1 vial) |
|---|---|---|
| Doxorubicin.HCl | 0.8 g | (10 mg) |
| Hydrochloric acid 0.1N q.s. to | pH = 3 | (pH = 3) |
| Water for injections q.s. to | 0.4 l | (5 ml) |

Doxorubicin.HCl (0.8 g) was dissolved in 90 percent of the amount of water for injections, de-aerated by nitrogen bubbling. The hydrochloric acid was then added dropwise to adjust the pH of the solution to 3. Further de-aerated water for injections was then added to bring the solution to its final volume (0.4 l).

The solution was filtered through a $0.22\mu$ microporous membrane under nitrogen pressure. Volumes of 5 ml of the solution were distributed into type I-colourless glass vials having 5/7 ml capacity. The vials ere then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatogrpahy (HPLC) for the determination of potency, are reported in the following Table 2:

TABLE 2

INITIAL VALUES

Concentration: 1.992 mg/ml
Relative % Assay: 100.0          pH = 3.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 1.995 | 100.2 | 1.952 | 98.0 | 1.919 | 96.3 | 1.493 | 75.0 |
| 2 | | | 1.889 | 94.8 | 1.851 | 92.9 | 1.036 | 51.9 |
| 3 | | | 1.876 | 94.2 | 1.565 | 78.6 | 0.730 | 36.7 |
| 4 | 1.979 | 99.4 | 1.808 | 90.8 | 1.393 | 69.9 | | |
| 12 | 1.972 | 99.0 | | | | | | |

$t_{90}$ (days) extrapolated according to Arrhenius equation:
$t_{90}$ at 4° C. = 3970 days
$t_{90}$ at 8° C. = 2000 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 3

| Composition | for 80 vials | (for 1 vial) |
|---|---|---|
| Doxorubicin.HCl | 8.0 g | (100 mg) |
| Hydrochloric acid 0.1N q.s. to | pH = 3 | (pH = 3) |
| Water for injections q.s. to | 0.4 l | (5 ml) |

Doxorubicin.HCl (8.0 g) was dissolve din 90 percent of the amount of water for injections, de-aerated by nitrogen bubbling. The hydrochloric acid was then added dropwise to adjust the pH of the solution to 3. Further de-aerated water for injections was then added to bring the solution to its final volume (0.4 l).

The solution was filtered through a $0.22\mu$ microporous membrane under nitrogen pressure. Volumes of 5 ml of the solution were distributed into type I-colourless glass vials having 5/7 ml capacity. The vials ere then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatogrpahy (HPLC) for the determination of potency, are reported in the following Table 3:

TABLE 3

INITIAL VALUES

Concentration: 20.06 mg/ml
Relative % Assay: 100.0          pH = 2.95

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 20.06 | 100.0 | 19.56 | 97.5 | 17.84 | 88.9 | 12.31 | 61.4 |
| 2 | | | 18.87 | 94.1 | 15.61 | 77.8 | 7.09 | 35.3 |
| 3 | | | 18.24 | 90.9 | 13.41 | 66.8 | 3.13 | 15.6 |
| 4 | 19.91 | 99.2 | 17.51 | 87.3 | 11.07 | 55.2 | | |
| 12 | 19.80 | 98.7 | | | | | | |

$t_{90}$ (days) extrapolated according to Arrhenius equation:
$t_{90}$ at 4° C. = 3700 days
$t_{90}$ at 8° C. = 1780 days Similar stability data can be observed also for analogous solutions containing 4'-epi-doxorubicin or 4'-desoxy-doxorubicin, as hydrochloride salts, at the same 20 mg/ml concentration.

EXAMPLE 4

| Composition | for 80 vials | (for 1 vial) |
|---|---|---|
| Doxorubicin.HCl | 0.80 g | (10.0 mg) |
| Polyvinylpyrrolidone | 20.00 g | (250.0 mg) |

| Composition | for 80 vials | (for 1 vial) |
|---|---|---|
| Water for injections q.s. to | 0.40 l | (5.0 ml) |

Doxorubicin.HCl (0.80 g) was dissolved in 90 percent of the amount of water for injections, de-aerated by nitrogen bubbling. The pH of the solution was not adjusted. Polyvinylpyrrolidone was added and dissolved under stirring and nitrogen bubbling. Further de-aerated water for injections was then added to bring the solution to its final volume (0.40 l).

The solution was filtered through a 0.22μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 4:

TABLE 4

INITIAL VALUES

Concentration: 1.986 mg/ml
Relative % Assay: 100.0      pH = 4.6

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % As-say | Conc. mg/ml | Rel. % As-say | Conc. mg/ml | Rel. % As-say | Conc. mg/ml | Rel. % As-say |
| 1 | 1.984 | 99.9 | 1.928 | 97.1 | 1.797 | 90.5 | 1.605 | 80.8 |
| 2 | | | 1.847 | 93.0 | 1.616 | 81.4 | 1.293 | 65.1 |
| 3 | | | 1.828 | 92.0 | 1.527 | 76.9 | 1.018 | 51.3 |
| 4 | 1.928 | 97.1 | 1.797 | 90.5 | 1.403 | 70.7 | | |
| 8 | 1.989 | 100.1 | | | | | | |

$t_{90}$ (days) extrapolated according to Arrhenius equation:
$t_{90}$ at 4° C. = 1460 days
$t_{90}$ at 8° C. = 835 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 5

| Composition | for 80 vials | (for 1 vial) |
|---|---|---|
| Doxorubicin.HCl | 0.800 g | (10.00 mg) |
| N,N-Dimethylacetamide | 0.060 l | (0.75 ml) |
| Propylene glycol | 0.048 l | (0.60 ml) |
| Ethanol | 0.012 l | (0.15 ml) |
| Hydrochloric acid 0.1N q.s. to | pH = 3 | (pH = 3) |
| Water for injections q.s. to | 0.400 l | (5.00 ml) |

Doxorubicin.HCl (0.800 g) was dissolved in 90 percent of the amount of water for injections, de-aerated by nitrogen bubbling. N,N-dimethylacetamide, proylene glycol and ethanol were subsequently added under stirring and nitrogen bubbling. The hydrochloric acid was then added dropwise to adjust the pH of the solution to 3. Further de-aerated water for injections was then added to bring the solution to its final volume (0.40 l).

The solution was filtered through a 0.22μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 5:

TABLE 5

INITIAL VALUES

Concentration: 2.000 mg/ml
Relative % Assay: 100.0      pH = 3.03

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % As-say | Conc. mg/ml | Rel. % As-say | Conc. mg/ml | Rel. % As-say | Conc. mg/ml | Rel. % As-say |
| 1 | | | 1.892 | 94.6 | 1.735 | 86.7 | 1.495 | 74.7 |
| 2 | 1.993 | 99.7 | 1.927 | 96.4 | 1.624 | 81.2 | 1.212 | 60.6 |
| 3 | | | 1.908 | 95.4 | 1.432 | 71.6 | 1.032 | 51.6 |
| 4 | 2.00 | 100.0 | 1.863 | 93.2 | 1.266 | 63.3 | | |
| 8 | 1.960 | 98.0 | | | | | | |

$t_{90}$ (days) extrapolated according to Arrhenius equation:
$t_{90}$ at 4° C. = 4360 days
$t_{90}$ at 8° C. = 2200 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 6

| Composition | for 80 vials | (for 1 vial) |
|---|---|---|
| Doxorubicin.HCl | 0.8 g | (10.0 mg) |
| Polyvinylpyrrolidone | 20.0 g | (250.0 mg) |
| Hydrochloric acid 0.1N q.s. to | pH = 3 | (pH = 3) |
| Water for injections q.s. to | 0.4 l | (5.0 ml) |

Doxorubicin.HCl (0.8 g) was dissolved in 90 percent of the amount of water for injections, de-aerated by nitrogen bubbling. Polyvinylpyrrolidone was added and dissolved under stirring and nitrogen bubbling. The hydrochloric acid was then added dropwise to adjust the pH of the solution to 3. Further de-aerated water for injections was then added to bring the solution to its final volume (0.40 l).

The solution was filtered through a 0.22 $\mu$ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 6:

TABLE 6

INITIAL VALUES

Concentration: 1.973 mg/ml
Relative % Assay: 100.0        pH = 2.71

| | \multicolumn{8}{c}{TEMPERATURE} | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 2.028 | 102.8 | 1.944 | 98.5 | 1.791 | 90.8 | 1.477 | 74.9 |
| 2 | | | 1.885 | 95.5 | 1.582 | 80.2 | 0.972 | 49.3 |
| 3 | | | 1.840 | 93.2 | 1.402 | 71.0 | 0.632 | 32.0 |
| 4 | 1.913 | 97.0 | 1.853 | 93.9 | 1.273 | 64.5 | | |
| 8 | 1.972 | 99.9 | | | | | | |

$t_{90}$ (days) extrapolated according to Arrhenius equation:
$t_{90}$ at 4° C. = 5560 days
$t_{90}$ at 8° C. = 2670 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 7

| Composition | for 80 vials | (for 1 vial) |
|---|---|---|
| Doxorubicin.HCl | 8.00 g | (100.0 mg) |
| N,N-Dimethylacetamide | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (8.00 g) was dissolved in 90 percent of the amount of water for injections, de-aerated by nitrogen bubbling. N,N-dimethylacetamide was added under stirring and nitrogen bubbling. The hydrochloric acid was then added dropwise to adjust the pH of the solution to 3. Further de-aerated water for injections was then added to bring the solution to its final volume (0.40 l).

The solution was filtered through a 0.22 $\mu$ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 7:

TABLE 7

INITIAL VALUES

Concentration: 19.32 mg/ml
Relative % Assay: 100.0        pH = 2.96

| | \multicolumn{8}{c}{TEMPERATURE} | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 20.1 | 103.5 | 19.14 | 99.1 | 17.34 | 89.8 | 15.57 | 80.6 |
| 2 | | | 19.20 | 99.4 | 15.77 | 81.6 | 12.94 | 67.0 |
| 3 | | | 18.06 | 93.5 | 14.85 | 76.9 | 11.61 | 60.1 |
| 4 | 20.03 | 103.7 | 17.81 | 92.2 | 13.78 | 71.3 | | |
| 8 | 19.99 | 103.5 | | | | | | |

$t_{90}$ (days) extrapolated according to Arrhenius equation:
$t_{90}$ at 4° C. = 1310 days
$t_{90}$ at 8° C. = 770 days Similar stability data can be observed also for analogous solutions containing 4'-epi-doxorubicin, 4'-desoxy-doxorubicin, as hydrochloride salts, at the same 20 mg/ml concentration.

EXAMPLE 8

| Composition | for 80 vials | (for 1 vial) |
|---|---|---|
| Doxorubicin.HCl | 0.80 g | (10.0 mg) |
| Ethanol | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (0.80 g) was dissolved in 90 percent of the amount of water for injections, de-aerated by nitrogen bubbling. Ethanol was added under stirring and nitrogen bubbling. Hydrochloric acid 0.1 N was then added dropwise to adjust the pH of the solution to 3. De-aerated water for injections was then added to bring the solution to its final volume (0.40 l).

The solution was filtered through a 0.22 μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 8:

TABLE 8

INITIAL VALUES

Concentration: 1.979 mg/ml
Relative % Assay: 100.0    pH = 3.11

TEMPERATURE

| TIME (weeks) | 4° C. Conc. mg/ml | 4° C. Rel. % Assay | 35° C. Conc. mg/ml | 35° C. Rel. % Assay | 45° C. Conc. mg/ml | 45° C. Rel. % Assay | 55° C. Conc. mg/ml | 55° C. Rel. % Assay |
|---|---|---|---|---|---|---|---|---|
| 1 | 2.010 | 101.6 | 1.965 | 99.3 | 1.947 | 98.4 | 1.750 | 88.4 |
| 2 | | | 1.957 | 98.9 | 1.910 | 96.5 | 1.645 | 83.1 |
| 3 | | | 1.895 | 95.8 | 1.737 | 87.8 | 1.356 | 68.5 |
| 4 | 1.927 | 97.3 | 1.818 | 91.9 | 1.678 | 84.8 | | |
| 12 | 1.939 | 97.9 | | | | | | |

$t_{90}$ (days) extrapolated according to Arrhenius equation:
$t_{90}$ at 4° C. = 1270 days
$t_{90}$ at 8° C. = 780 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 9

| Composition | for 80 vials | (for 1 vial) |
|---|---|---|
| Doxorubicin.HCl | 8.000 g | (100.00 mg) |
| N,N-Dimethylacetamide | 0.060 l | (0.75 ml) |
| Propylene glycol | 0.048 l | (0.60 ml) |
| Ethanol | 0.012 l | (0.15 ml) |
| Hydrochloric acid 0.1N q.s. to | pH = 3 | (pH = 3) |
| Water for injections q.s. to | 0.400 l | (5.00 ml) |

Duxorubicin.HCl (8.000 g) was dissolved in 90 percent of the amount of water for injections, de-aerated by nitrogen bubbling. N,N-dimethylacetamide, propylene glycol and ethanol were subsequently added under stirring and nitrogen bubbling. The hydrochloric acid was then added dropwise to adjust the pH of the solution to 3. Further de-aerated water for injections was then added to bring the solution to its final volume (0.400 l).

The solution was filtered through a 0.22μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials were tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 9:

TABLE 9

INITIAL VALUES

Concentration: 20.07 mg/ml
Relative % Assay: 100.0    pH = 2.99

TEMPERATURE

| TIME (weeks) | 4° C. Conc. mg/ml | 4° C. Rel. % Assay | 35° C. Conc. mg/ml | 35° C. Rel. % Assay | 45° C. Conc. mg/ml | 45° C. Rel. % Assay | 55° C. Conc. mg/ml | 55° C. Rel. % Assay |
|---|---|---|---|---|---|---|---|---|
| 1 | | | 19.14 | 95.4 | 17.81 | 88.7 | 14.84 | 73.9 |
| 2 | 19.97 | 99.5 | 19.07 | 95.0 | 16.27 | 81.1 | 12.36 | 61.6 |
| 3 | | | 18.08 | 90.1 | 14.62 | 72.9 | 10.04 | 50.0 |
| 4 | 20.06 | 99.9 | 18.03 | 89.8 | 13.20 | 65.8 | | |
| 8 | 19.69 | 98.1 | | | | | | |

$t_{90}$ (days) extrapolated according to Arrhenius equation:
$t_{90}$ at 4° C. = 846 days
$t_{90}$ at 8° C. = 505 days Similar stability data can be observed for analogous solutions containing 4'-epi-doxorubicin or 4'-desoxy-doxorubicin, as hydrochloride salts, at the same 20 mg/ml concentration.

EXAMPLE 10

| Composition | for 80 vials | (for 1 vial) |
|---|---|---|
| Doxorubicin.HCl | 8.0 g | (100.0 mg) |
| Polyvinylpyrrolidone | 20.0 g | (250.0 mg) |
| Hydrochloric acid 0.1N q.s. to | pH = 3 | (pH = 3) |
| Water for injections q.s. to | 0.4 l | (5.0 ml) |

Doxorubicin.HCl (8.0 g) was dissolved in 90 percent of the amount of water for injections, de-aerated by nitrogen bubbling. Polyvinylpyrrolidone was added and dissolved under stirring and nitrogen bubbling. The hydrochloric acid was then added dropwise to adjust the pH of the solution to 3. Further de-aerated water for injections was then added to bring the solution to its final volume (0.4 l).

The solution was filtered through a 0.22µ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 10:

TABLE 10

INITIAL VALUES

Concentration: 19.57 mg/ml
Relative % Assay: 100.0         pH = 2.62

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 19.54 | 99.9 | 19.11 | 97.6 | 16.88 | 86.2 | 12.48 | 63.8 |
| 2 | | | 18.43 | 94.2 | 14.13 | 72.2 | 6.00 | 30.7 |
| 3 | | | 18.02 | 92.1 | 11.57 | 59.1 | 2.61 | 13.3 |
| 4 | 19.58 | 100.1 | 17.36 | 88.7 | 9.23 | 47.2 | | |
| 8 | 19.34 | 98.8 | | | | | | |

$t_{90}$ (days) extrapolated according to Arrhenius equation:
$t_{90}$ at 4° C. = 2540 days
$t_{90}$ at 8° C. = 1290 days Similar stability data can be observed for analogous solutions containing 4'-epi-doxorubicin or 4'-desoxy-doxorubicin, as hydrochloride salts, at the same 20 mg/ml concentration.

EXAMPLE 11

| Composition | for 80 vials | (for 1 vial) |
|---|---|---|
| Doxorubicin.HCl | 0.80 g | (10.0 mg) |
| N,N-Dimethylacetamide | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (0.80 g) was dissolved in 90% of the amount of water for injections, de-aerated by nitrogen bubbling. N,N-Dimethylacetamide was added under stirring and nitrogen bubbling. Hydrochloric acid 0.1N was then added dropwise to adjust the pH of the solution to 3. De-aerated water for injections was finally added to bring the solution to its final volume (0.40 l).

The solution was filtered through a 0.22µ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 11:

TABLE 11

INITIAL VALUES

Concentration: 1.826 mg/ml
Relative % Assay: 100.0         pH = 3.14

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 1.830 | 100.2 | 1.812 | 99.2 | 1.784 | 97.7 | 1.605 | 87.9 |
| 2 | 1.818 | 99.6 | 1.781 | 97.5 | 1.554 | 85.1 | 1.292 | 70.8 |
| 3 | | | 1.743 | 95.4 | 1.409 | 77.2 | 1.018 | 55.7 |
| 4 | 1.823 | 99.8 | 1.734 | 95.0 | 1.369 | 75.0 | | |
| 8 | 1.792 | 98.2 | | | | | | |

$t_{90}$ (days) extrapolated according to Arrhenius equation:
$t_{90}$ at 4° C. = 5815 days
$t_{90}$ at 8° C. = 2920 days Similar stability data can be observed also for analogous solutions containing either doxorubicin hydrochloride at 5 mg/ml concentration, or 4'-epi-doxorubicin, 4'-desoxy-doxorubicin, 4'-epi-desoxy-4'-iodo-doxorubicin, daunorubicin or 4-demethoxy-deunorubicin, as hydrochloride salts, at both 2 mg/ml and 5 mg/ml concentration.

EXAMPLE 12

| Composition | for 80 vials | (for 1 vial) |
|---|---|---|
| Doxorubicin.HCl | 0.80 g | (10.0 mg) |
| Propylene glycol | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (0.80 g) was dissolved in 90% of the amount of water for injections de-aerated by nitrogen bubbling. Propylene glycol was added under stirring and nitrogen bubbling. Hydrochloric acid 0.1N was then added dropwise to adjust the pH of the solution to 3. De-aerated water for injections was finally added to bring the solution to its final volume (0.40 l).

The solution was filtered through a 0.22µ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 4 weeks (4° C.).

The stability data obtained, using high performance liquid chromatography (HPLC) for the determination of potency, are reported in the following Table 12:

TABLE 12

INITIAL VALUES

Concentration: 1.982 mg/ml
Relative % Assay: 100.0     pH = 3.11

TEMPERATURE

| TIME (weeks) | 4° C. Conc. mg/ml | 4° C. Rel. % Assay | 35° C. Conc. mg/ml | 35° C. Rel. % Assay | 45° C. Conc. mg/ml | 45° C. Rel. % Assay | 55° C. Conc. mg/ml | 55° C. Rel. % Assay |
|---|---|---|---|---|---|---|---|---|
| 1 | 1.972 | 99.5 | 1.934 | 97.6 | 1.889 | 95.3 | 1.705 | 86.0 |
| 2 | | | 1.952 | 98.5 | 1.795 | 90.6 | 1.483 | 74.8 |
| 3 | | | 1.935 | 97.6 | 1.699 | 85.7 | 1.153 | 58.2 |
| 4 | 2.056 | 103.7 | 1.788 | 90.2 | 1.460 | 73.7 | | |

$t_{90}$ (days) extrapolated according to Arrhenius equation:
$t_{90}$ at 4° C. = 1794 days
$t_{90}$ at 8° C. = 1025 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml 5 mg/ml concentration.

EXAMPLE 13

| Composition | for 80 vials | (for 1 vial) |
|---|---|---|
| Doxorubicin.HCl | 0.80 g | (10.0 mg) |
| Polyethylene glycol 400 | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (0.80 g) was dissolved in 90% of the amount of water for injections, de-aerated by nitrogen bubbling. Polyethylene glycol 400 was added under stirring and nitrogen bubbling. Hydrochloric acid 0.1N was then added dropwise to adjust the pH of the solution to 3. De-aerated water for injections was finally added to bring the solution to its final volume (0.40 l).

The solution was filtered through a 0.22µ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 4 weeks (4° C.).

The stability data obtained, using high performance liquid chromatography (HPLC) for the determination of potency, are reported in the following Table 13:

TABLE 13

INITIAL VALUES

Concentration: 1.907 mg/ml
Relative % Assay: 100.0     pH = 3.07

TEMPERATURE

| TIME (weeks) | 4° C. Conc. mg/ml | 4° C. Rel. % Assay | 35° C. Conc. mg/ml | 35° C. Rel. % Assay | 45° C. Conc. mg/ml | 45° C. Rel. % Assay | 55° C. Conc. mg/ml | 55° C. Rel. % Assay |
|---|---|---|---|---|---|---|---|---|
| 1 | 1.871 | 98.1 | 1.797 | 94.2 | 1.668 | 87.5 | 1.484 | 77.8 |
| 2 | | | 1.710 | 89.7 | 1.608 | 84.3 | 1.237 | 64.9 |
| 3 | | | 1.739 | 91.2 | 1.551 | 81.3 | 1.007 | 52.8 |
| 4 | 1.873 | 98.2 | 1.693 | 88.8 | 1.453 | 76.2 | | |

$t_{90}$ (days) extrapolated according to Arrhenius equation:
$t_{90}$ at 4° C. = 1130 days
$t_{90}$ at 8° C. = 680 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 14

| Composition | for 80 vials | (for 1 vial) |
|---|---|---|
| Doxorubicin.HCl | 0.8 g | (10 mg) |
| Hydrochloric acid 0.1N q.s. to | pH = 3 | (pH = 3) |
| Water for injections q.s. to | 0.4 l | (5 ml) |

Doxorubicin.HCl (0.8 g) was dissolved in 90 percent of the amount of water for injections, de-aerated by nitrogen bubbling. The hydrochloric acid was then added dropwise to adjust the pH of the solution to 3. Further de-aerated water for injections was then added to bring the solution to its final volume (0.4 l).

The solution was filtered through a 0.22μ microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 4° C. and 8° C. for up to 6 months.

The stability data obtained, using high performance liquid chromatography (HPLC) for the determination of potency, are reported in the following Table 14:

TABLE 14

INITIAL VALUES

Concentration: 2.039 mg/ml
Relative % Assay: 100.0    pH = 3.06

| | TEMPERATURE | | | |
|---|---|---|---|---|
| | 4° C. | | 8° C. | |
| TIME (months) | Conc. mg/ml | Rel. % Assay | Conc. mg/ml | Rel. % Assay |
| 1 | 1.983 | 97.3 | 1.959 | 96.1 |
| 3 | 1.984 | 97.3 | 1.983 | 97.3 |
| 6 | 2.012 | 98.7 | 2.002 | 98.2 |

At the same conditions, similar stability data can be generally observed also for the other solutions mentioned in the preceding examples.

What is claimed is:

1. A physiologically acceptable solution of epirubicin hydrochloride dissolved in a physiologically acceptable aqueous solvent, having a pH adjusted to from 2.5 to 5.0 with a physiologically acceptable acid selected from the group consisting of hydrochloric acid, sulfuric acid, phosphoric acid, methane sulfonic acid, and tartaric acid, the concentration of said epirubicin hydrochloride being from 0.1 to 100 mg/ml, wherein said solution is contained in a sealed container.

2. The solution of claim 1 wherein said physiologically acceptable aqueous solvent is selected from the group consisting of water, ethanol, polyethylene glycol, N.N.-dimethylacetamide, and mixtures thereof.

3. The solution of claim 1 wherein the physiologically acceptable aqueous solvent is water.

4. The solution of claim 1 wherein the concentration of epirubicin hydrochloride ranges from 0.1 to 50 mg/ml.

5. The solution of claim 4 wherein the concentration of epirubicin hydrochloride ranges from 1 to 20 mg/ml.

6. The solution of claim 1 wherein the concentration of epirubicin hydrochloride is about 2 mg/ml.

7. The solution of claim 1 wherein the concentration of epirubicin hydrochloride is about 5 mg/ml.

8. The solution of claim 1 further comprising a tonicity adjusting agent.

9. The epirubicin hydrochloride solution of claim 1, wherein said solution exhibits storage stability as a result of said pH being adjusted to the said pH range using said acids.

10. The solution of claim 1 wherein the concentration of epirubicin hydrochloride is about 1 mg/ml.

11. The solution of claim 1 wherein the physiologically acceptable acid is hydrochloric acid.

12. A physiologically acceptable aqueous solution of epirubicin hydrochloride dissolved in a physiologically acceptable solvent, having a pH adjusted from 2.5 to 5.0 with a physiologically acceptable acid selected from the group consisting of hydrochloric acid, sulfuric acid, phosphoric acid, methanesulfonic acid, and tartaric acid, the concentration of said epirubicin hydrochloride being from 0.1 to 100 mg/ml.

13. The solution of claim 12, wherein said solution exhibits storage stability as a result of said pH being adjusted to the said pH range using said acids.

14. The solution of claim 12 wherein the concentration of epirubicin hydrochloride is about 1 mg/ml.

15. The solution of claim 14 wherein the physiologically acceptable acid is hydrochloric acid.

16. A physiologically acceptable aqueous solution of anthracycline glycoside selected from the group consisting of idarubicin hydrochloride, doxorubicin hydrochloride and epirubicin hydrochloride dissolved in a physiologically acceptable solvent, having a pH adjusted from 2.5 to 5.0 with a physiologically acceptable acid selected from the group consisting of hydrochloric acid, sulfuric acid, phosphoric acid, methanesulfonic acid, and tartaric acid, the concentration of said anthracycline glycoside being from 0.1 to 100 mg/ml.

17. The solution of claim 16 wherein said solution exhibits storage stability as a result of said pH being adjusted to said pH range using said acids.

18. The solution of claim 16 wherein the concentration of anthracycline glycoside is about 1 mg/ml.

19. The solution of claim 18 wherein the physiologically acceptable acid is hydrochloric acid.

* * * * *